(12) United States Patent
Harper

(10) Patent No.: US 6,824,265 B1
(45) Date of Patent: Nov. 30, 2004

(54) ILLUMINATED SAFETY AND WORK GLASSES

(76) Inventor: Wesley Stephen Harper, 717 Rose St., Craig, CO (US) 81625

( * ) Notice: Subject to any disclaimer, the term of this patent is extended or adjusted under 35 U.S.C. 154(b) by 20 days.

(21) Appl. No.: 10/404,764

(22) Filed: Mar. 31, 2003

(51) Int. Cl.$^7$ ................................................. G02C 1/00
(52) U.S. Cl. ...................................................... 351/158
(58) Field of Search .............................. 351/41, 51, 52, 351/158

(56) References Cited

U.S. PATENT DOCUMENTS

| | | | |
|---|---|---|---|
| 4,254,451 A | * | 3/1981 | Cochran, Jr. ................. 362/103 |
| 4,283,127 A | | 8/1981 | Rosenwinkel et al. |
| 4,822,160 A | | 4/1989 | Tsai |
| 4,822,161 A | * | 4/1989 | Jimmy ........................ 351/158 |
| 4,959,760 A | | 9/1990 | Wu |
| 5,224,772 A | | 7/1993 | Fustos |
| 5,230,558 A | | 7/1993 | Jong |
| D349,123 S | | 7/1994 | Cooley et al. |
| 5,722,762 A | | 3/1998 | Soll |
| D428,431 S | | 7/2000 | Jordan |
| 6,612,696 B2 | * | 9/2003 | Waters ........................ 351/158 |
| 2001/0021108 A1 | | 9/2001 | Shimada et al. |
| 2003/0086053 A1 | | 5/2003 | Waters |
| 2003/0206269 A1 | | 11/2003 | Waters |

FOREIGN PATENT DOCUMENTS

| | | |
|---|---|---|
| FR | 2 601 149 | 1/1988 |
| JP | 9017204 | 1/1997 |

* cited by examiner

*Primary Examiner*—Huy Mai

(57) ABSTRACT

An illuminated safety/work glasses device (202) utilizing light emitting diodes embedded into a one-piece flexible array (101) mounted to the left and right side of the lens (102). The light emitting diodes are positioned to the left and right, and above and below the wearer's eyes and may be powered through use of rechargeable powered earpieces (103 and 111) or remote battery pack (207).

10 Claims, 11 Drawing Sheets

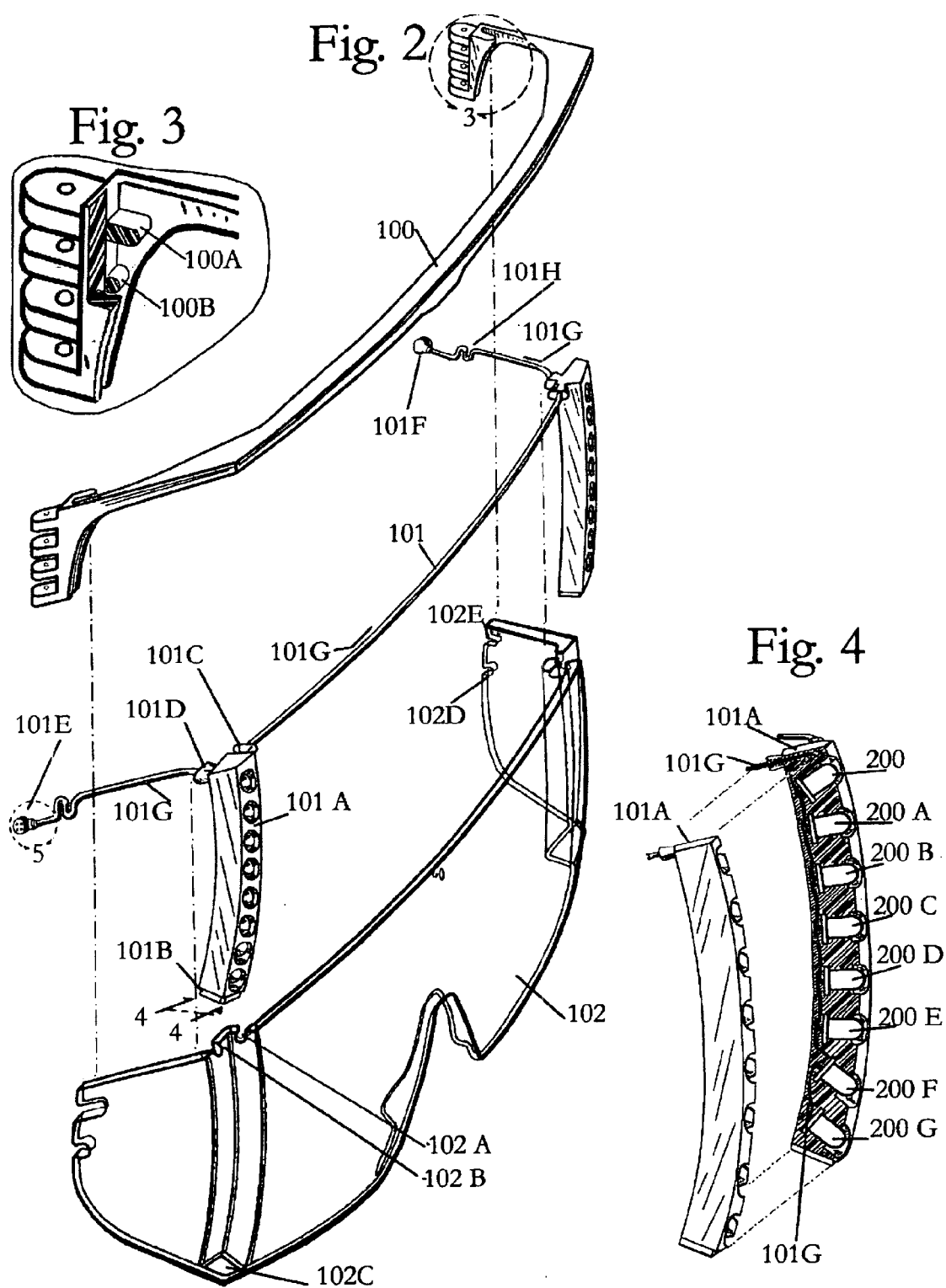

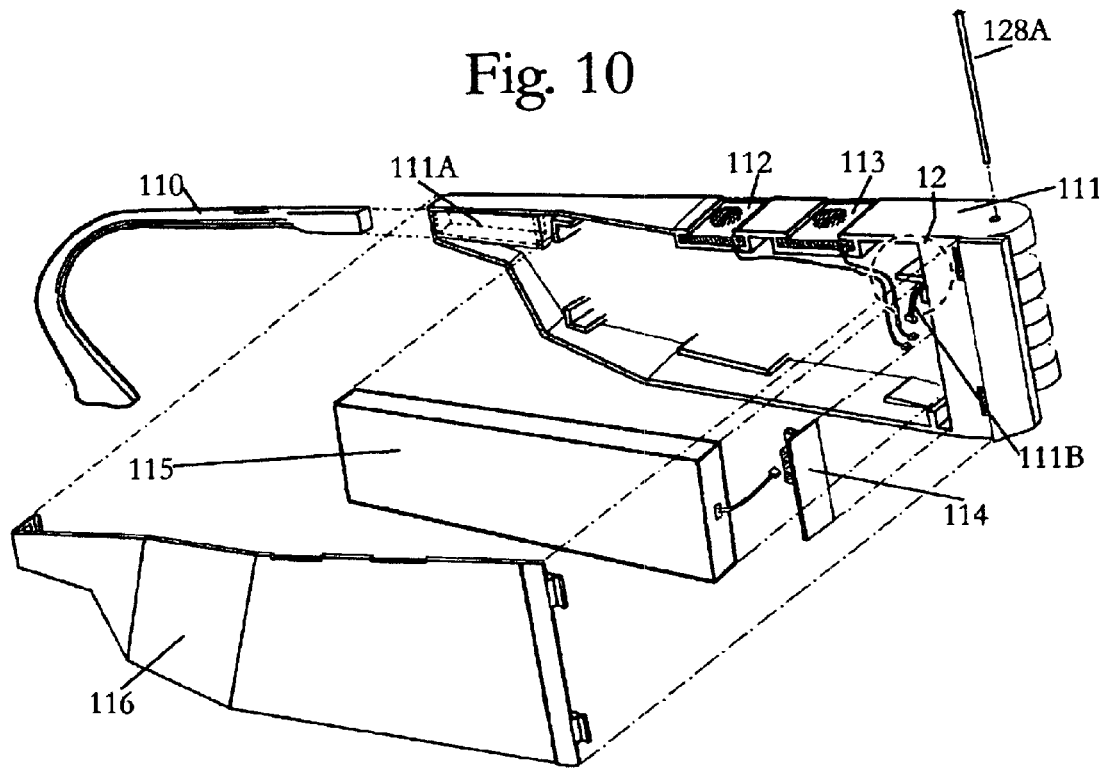
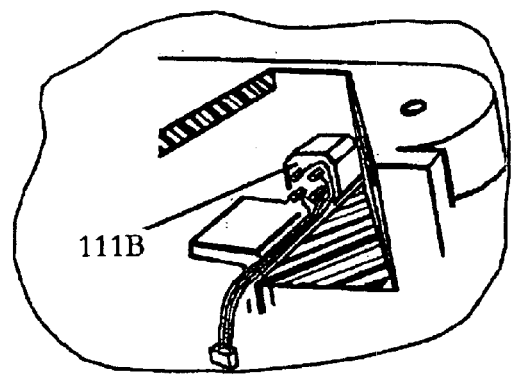

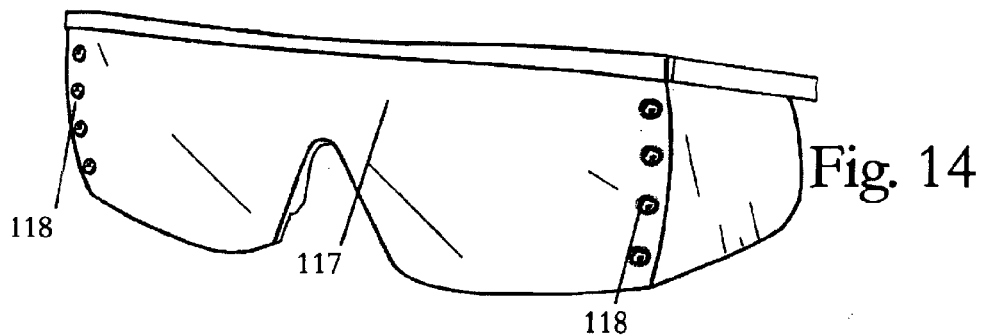
Fig. 14
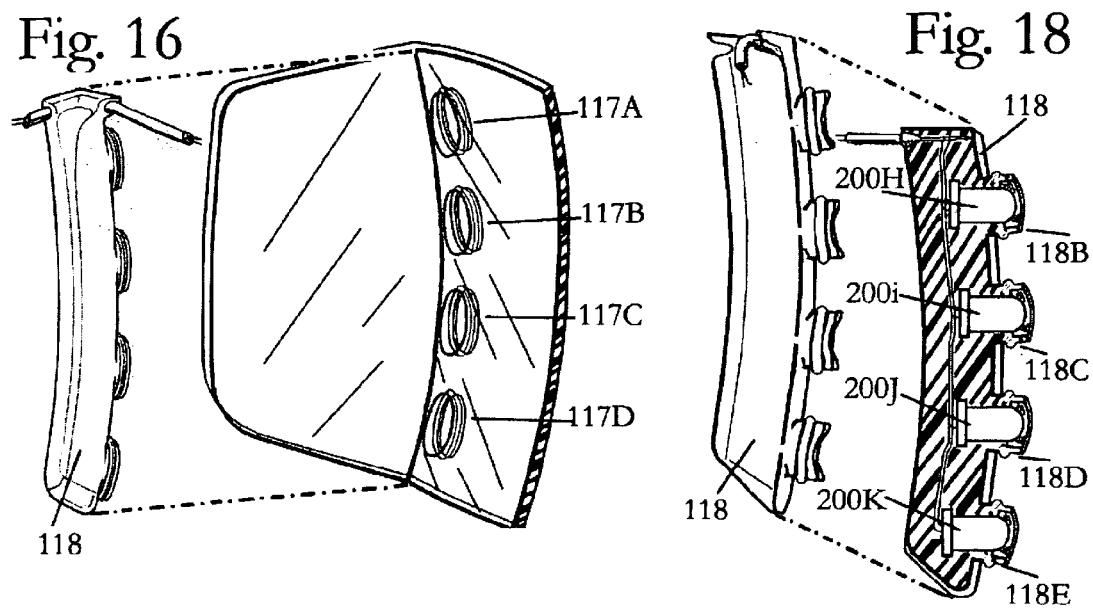
Fig. 16
Fig. 18
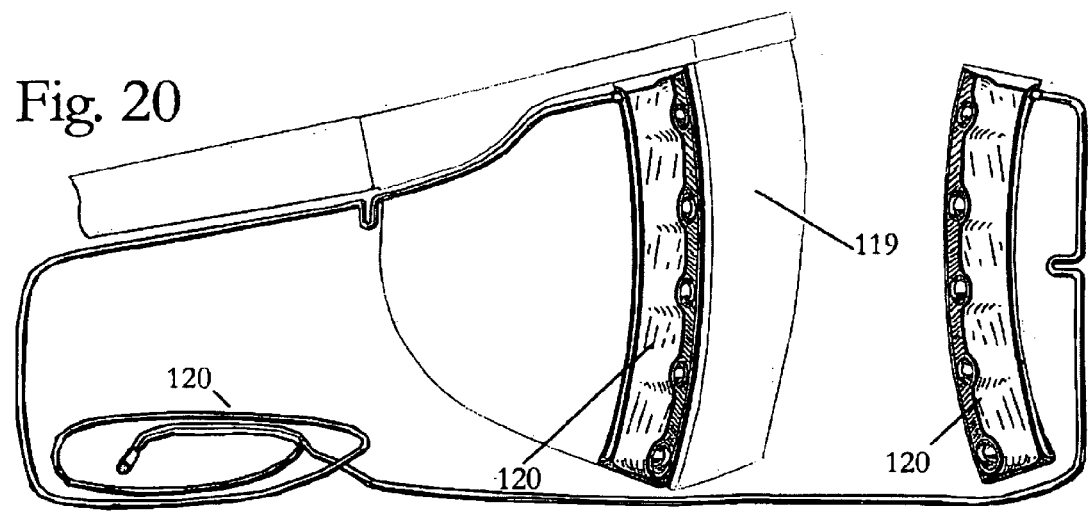
Fig. 20

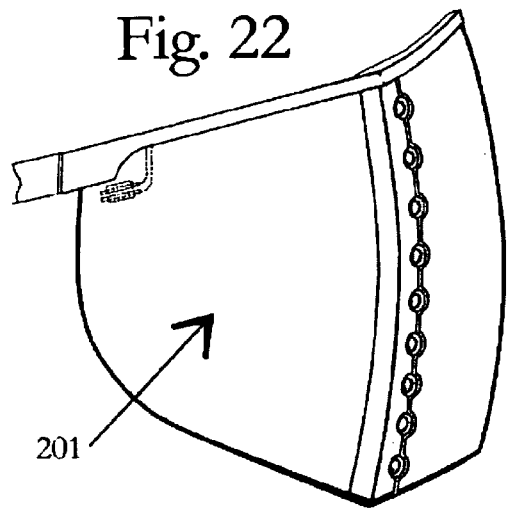
Fig. 22
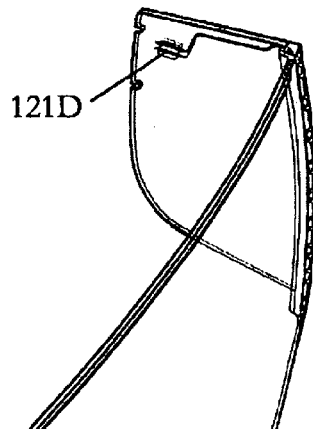
Fig. 24
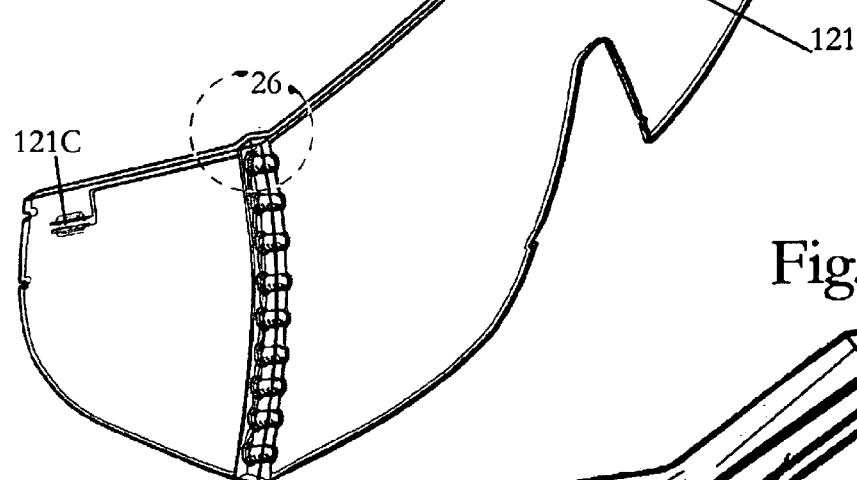
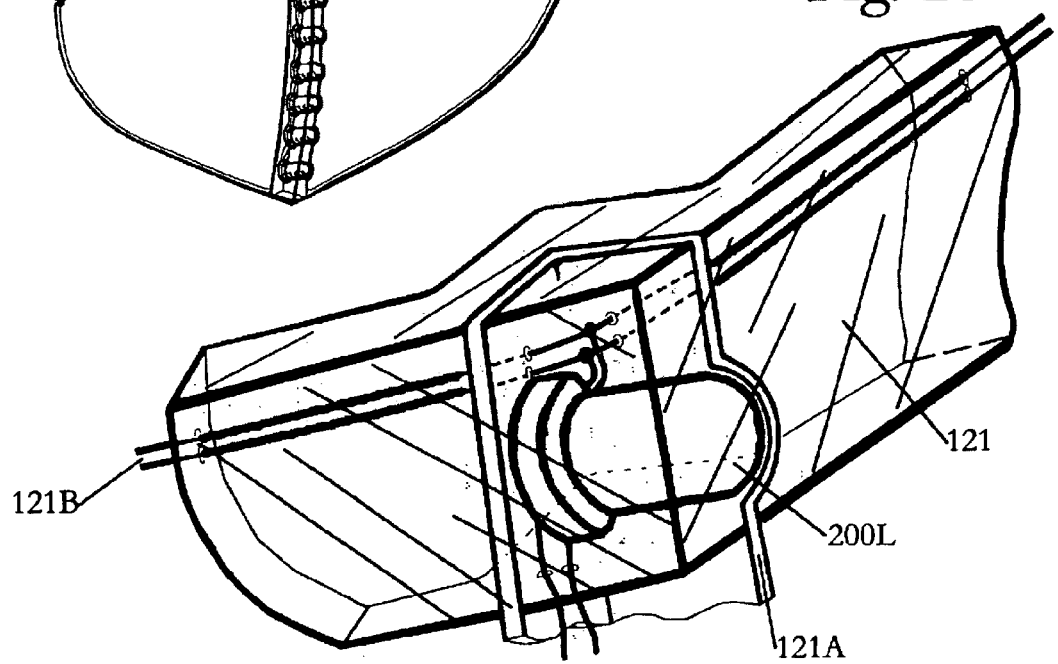
Fig. 26

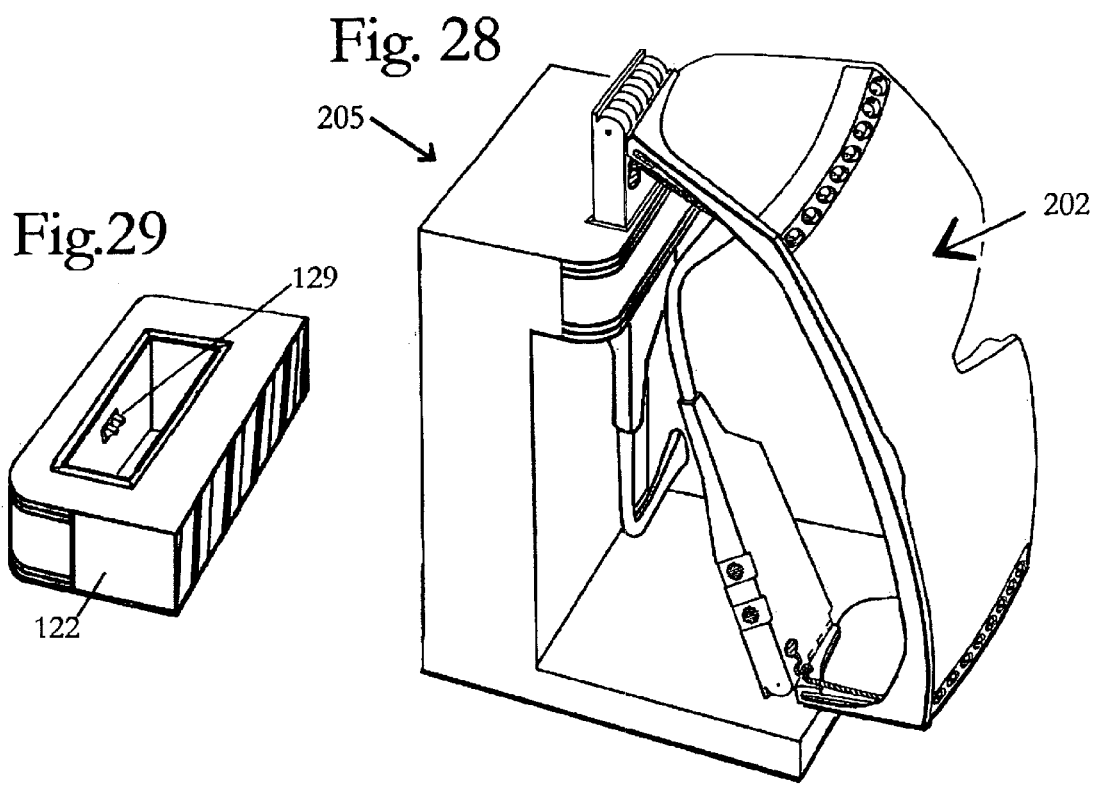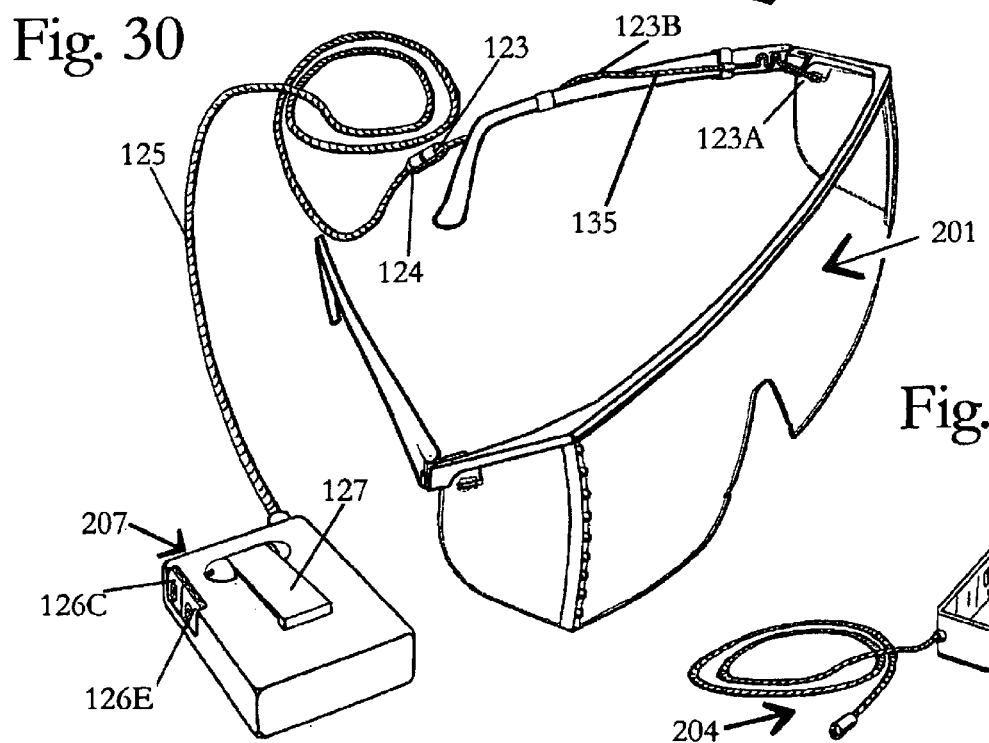

ILLUMINATED SAFETY AND WORK GLASSES

CROSS-REFERENCE TO RELATED INVENTIONS

Not Applicable

FEDERALLY SPONSORED RESEARCH

Not Applicable

SEQUENCE LISTING OR PROGRAM

Not Applicable

BACKGROUND OF THE INVENTION—FIELD OF INVENTION

This invention relates to head worn illuminating devices, more specifically to illuminating spectacles utilizing light emitting diodes as the light source.

BACKGROUND OF THE INVENTION

Presently existing electrically powered head worn illuminating devices are produced mainly in the form of headlamps. Less common is a design that successfully combines glasses and illumination as a single device.

Examples of light emitting diode-equipped glasses have been envisioned and manufactured but most designs are novelty devices and are not meant for illumination. U.S. Pat. No. 4,283,127 to Rosenwinkel et al (1981) discloses a pair of novelty flashing spectacles utilizing diodes mounted in the lens area. Another example of led-equipped glasses is U.S. Pat. No. 4,822,160 to Tsai (1989 containing a plurality of leds from left to right on the upper portion of the glasses. These glasses are designed to attract attention to the wearer by flashing and are not meant to provide area illumination.

Another type of head worn illuminating device comprises a dive mask with a plurality of lamps mounted along the top of the mask. U.S. Pat. No. 5,224,772 to Fustos (1993) discloses this design where a plurality of lamps on the top of the mask are flush mounted in an enclosure. A drawback to this design is shadowing of a portion of illuminated areas. This is caused by placement of the lights above the plane of the wearer's eyes. Obviously, the intended use is specific to underwater illumination, not general use.

Single and multiple point light source designs utilizing a filament bulb or bulbs are present. Drawbacks to this type of design can include high power consumption, poor color comprehension, and need for a reflector to focus the light into a useful beam. High power consumption is a disadvantage when the power source is limited as is the case when using batteries. The low efficiency of this type of system can result in short operational duration and can become costly due to need for frequent battery replacement. The light produced by these filament type bulbs is not a balanced white light and may not provide accurate color comprehension. Reflector assemblies and bulb sockets appear to be common components of designs employing filament bulbs and can add to the complexity, weight, and expense of designs of this type. U.S. Pat. No. 4,959,760 to Wu (1990) discloses use of an assembly fitted with a filament type bulb and made to attach to one earpiece of a pair of glasses. This design has the drawback of the light source emanating from only one point, the device mounted to the left only or right only extent of the glasses and can cause shadowing of viewed objects. The type of illuminating device used is a filament type bulb. This system shares the drawbacks of a filament bulb system. Additionally, modification of glasses is necessary in order to mount the assembly.

A design combining light emitting diodes and goggles is shown in U.S. Patent Application Publication US2001/0021108A1 for Shimada et al. (2001). FIGS. 9 and 10 of the application publication depict a set of goggles with 2 light emitting diode panels located behind the lens, each mounted in the left and right extent of the goggle frame. In use, the panels will be in very close proximity to the wearer's face. This creates an opportunity for injury to the wearer if the goggles are struck or otherwise forced towards the wearer's face. The rigidity of circuit boards mounted in or on the goggles may alter the flexibility built into the goggles. Under extreme impact, the circuit board may shatter and cause considerable injury to the wearer. Another shortfall in this design is risk caused from using uncovered and electrically unshielded circuit boards. If used in close proximity to ignitable vapors, a spark resulting from a shorted connection on the board could initiate a fire or explosion. Additionally, the led panels are quite large and may substantially interfere with or reduce forward vision and the apparent lack of light shielding around the led panels may allow a large amount of the emitted light to reflect back into the wearer's eyes. In actual use, this design could reduce the quality of vision, when compared to using unlighted goggles.

A design combining glasses and lamps as a single device is shown in RE'PUBLIQUE FRANCAISE patent 2 601 149 to Jean Jacques Koubi (1985). This design uses two filament type lamps, 1 located at each the left and right extent of the frames. For reasonably effective duration of operation, the low efficiency of the filament lamps may require a substantial power supply. Furthermore, the electrical conducting assembly (the subject of the patent) is exposed at the point where the frames meet the lens assembly and this type of design can create an exposed electrical arc, a definite hazard when used in areas containing ignitable vapors.

Briefly mentioned above is a difficulty in designing head worn lighting devices that becomes apparent when the device is used for certain tasks. This difficulty, a problem for designers of lighted headwear, is the shading of some areas the illuminating device is supposed to illuminate. Any single-point light source can cause shading if the light source is on a different plane than the viewer's eyes. Only true ambient light eliminates shading. However, it is possible to overcome this problem when designing head worn lighting by placing a plurality of forward emanating light sources to the left and right, and above and below the eyes of the viewer. This positioning provides light on all planes and sides of the object viewed and mimics, for the viewer, ambient light.

"Another design combining glasses and lamps is disclosed by Jordan in U.S. Pat. Des. No. 428,431 (2000). This design shows an eyeglass frame with four lamps mounted in the top portion of the frame. The electrical wiring is permanently embedded within the frame and it appears that the lamps are also permanently embedded within the frame. As discussed above, a shortcoming of this design is the potential of shading caused by placement of the lamps in a plane above the user's eyes. Also, from the apparent small size of the battery compartment, it appears that the glasses are not meant for long-duration operation. Due to the apparent small battery size, frequent battery replacement could become a costly drawback in actual use of this design."

Designs of head worn lighting devices will always cause some shadowing of the viewed object if lighting from a single point, or even multiple points if the light sources do not 'surround' the eyes of the viewer (above and below, and to the left and right). The closer the object being viewed is to the eyes, the more pronounced the shadowing will be. For certain types of close viewing, tasks such as stitching wounds, small parts fabrication, measurement and layout of small parts, watch and jewelry repair, sewing, etc. . . . can be more difficult to perform and reduce the accuracy of the task being done when this shading is present.

"FIGS. 2–6 of U.S. patent application publications US2003/0086053 and US2003/0206269 of Waters (2003) disclose another design where two compartments, one attached beyond the left extent, and one attached beyond the right extent of the glasses; each compartment having a diode mounted approximately at the center (elevation) of the glasses. Disadvantages of this design include: the 'plane' of illumination does not surround the users eyes and is in balance only when user's pupils are aligned with the diodes in reference to an object being viewed. Normal eye movement causing the pupils to move below or above this alignment, or 'plane', create a shading potential. Insignificant when viewing flat surfaces; but becoming a potentially significant negative factor when viewing three-dimensional surfaces such as found in the above-mentioned examples. The compartments individually contain two disc shaped batteries, a switch and the circuitry to connect the batteries and switch to the light emitting diode; shaped very similar to presently available 'key chain' LED lights. Illumination is from the left and right planes only, and top/bottom shadowing reducing accuracy of tasks being done can occur. There are no sealing devices shown where the diodes and the switches protrude from the compartments, or between the compartments and their screw-attached covers. With no provision for inhibiting liquids and gasses from making contact with the electrical components and connections, the compartments are not airtight and can be an ignition source for flammable and explosive liquids and gasses. There is no provision other than the batteries for providing power to the light emitting diodes; cost of replacement batteries could become a negative factor if used frequently. The compartments project outward from the exterior of the glasses, increasing the potential of physical interference. If a user were to fall or be struck in such a way that the compartment were forced into the user's head, the compartment and mounting devices of the compartment can increase risk of injury to user by magnifying and concentrating the force of the impact."

Japanese patent JP9017204 to Isobe Hitoshi (1997) discloses a led illumination system comprising an assembly that attaches to the earpieces of eyeglasses. This device consists of two assemblies, one attaching to the left extent and one attaching to the right extent of the frames. Each assembly contains one forward illuminating led. The disadvantage of this design is the placement of the leds. The leds are mounted above the plane of the eyes of the wearer and may cause shadowing.

Another design combining glasses and lamps as a single device is shown in U.S. Pat. Des. No. 349,123 to Cooley et al. (1994). This design uses 2 filament type lamps, with each lamp located at the left and right extent of the frames and on a plane above the wearer's eyes. The drawbacks of a filament bulb system apply to this design. Additionally, the lamp placement is in a plane above the eyes and shadowing can occur.

Other designs that place one lamp each at the left and right extent of the frames include U.S. Pat. No. 5,230,558 to Jong (1993) and U.S. Pat. No. 5,722,762 to Soll (1998). Both of these designs have spectacle-like frames containing the illuminating devices. Both designs may require the use of reflectors in order to generate a concentrated beam of light. Both designs do not contain a lens to protect the eyes and are meant for illumination only.

BACKGROUND OF THE INVENTION—OBJECTS AND ADVANTAGES

Several objects and advantages of the present invention are:

(a) to provide illuminating safety glasses using a plurality of light emitting diodes as the light source;

(b) to provide illuminating safety glasses, increasing accuracy and reducing difficulty of certain tasks by eliminating shaded areas, this done by positioning on the device light emitting diodes beyond either extents and above and below of the eyes of the wearer;

(c) to provide illuminating safety glasses in which the light emitting diodes are not mounted on circuit boards, but rather the light emitting diodes are encased in a flexible material along with their interconnecting electrical connections and electrical connectors in order to produce a simpler and flexible one piece array;

(d) to provide illuminating safety glasses in which the light emitting diode array is electrically shielded, inhibits liquids and gasses from electrical connections, and is capable of absorbing physical shock;

(e) to provide illuminating safety glasses in which the light emitting diode array is formed in such a manner as to require a minimum of mounting devices for attachment;

(f) to provide illuminating safety glasses in which the array assemblies may be powered by conventional or rechargeable batteries contained within one or both earpieces;

(g) to provide illuminating safety glasses that, when fitted with earpieces containing batteries, the earpieces are electrically shielded, inhibit liquids and gasses from their interior, and absorb physical shock;

(h) to provide illuminating safety glasses that, when fitted with earpieces containing batteries, may be stored and recharged through use of a cradle recharging device or recharged through use of any suitable recharging device;

(i) to provide illuminating safety glasses that, when not fitted with powered earpieces, may be powered through use of a battery pack containing conventional or rechargeable batteries;

(j) to provide illuminating safety glasses that are electrically controllable by circuitry contained within the power source assembly(s).

Further objects and advantages are to provide illuminating safety glasses which can replace conventional lighting devices in situations where it is advantageous, necessary, or safest to use both hands for the task. Still further objects and advantages will become apparent from a consideration of the ensuing description and drawings.

SUMMARY

In accordance with the present invention, my illuminating safety glasses comprises a lens, a light emitting diode array, frame, earpieces, an electrical control apparatus and a power source.

DRAWINGS—FIGURES

FIG. 2 is an exploded view of lens, array, and frame.

FIG. 3 is a magnified cutaway view of lens connecting lugs.

FIG. 4 is a cross section of the right portion of the external array taken along lines 4—4 of FIG. 2.

FIG. 10 is an exploded view of the right powered earpiece.

FIG. 12 is a magnified cutaway view to show the recessed output jack.

FIG. 14 is a perspective view of another embodiment of the present invention utilizing internally located lighting arrays.

FIG. 16 is an exploded view illustrating the left internal array section and how it attaches to lens.

FIG. 18 is a cutaway view of the left internal array section to show shape of the connecting bezel sections.

FIG. 20 shows an example of another embodiment of the present invention present as an external temporarily mounted array.

FIG. 22 is another embodiment of my invention showing a right view of the embodiment.

FIG. 24 is a perspective view of the array embedded lens.

FIG. 26 is a magnified view showing components embedded within the lens.

FIG. 28 is a perspective view of a type of cradle charger assembly for use with the powered earpieces.

FIG. 29 is a cutaway view of the section of the cradle charger housing the protruding electrical charging connector.

FIG. 30 is a perspective view of a type of battery pack assembly for use with the illuminated safety glasses.

FIG. 31 is a perspective view of another type of recharging and power connector for powered earpiece.

Drawings -- Reference Numerals

Figure 1:
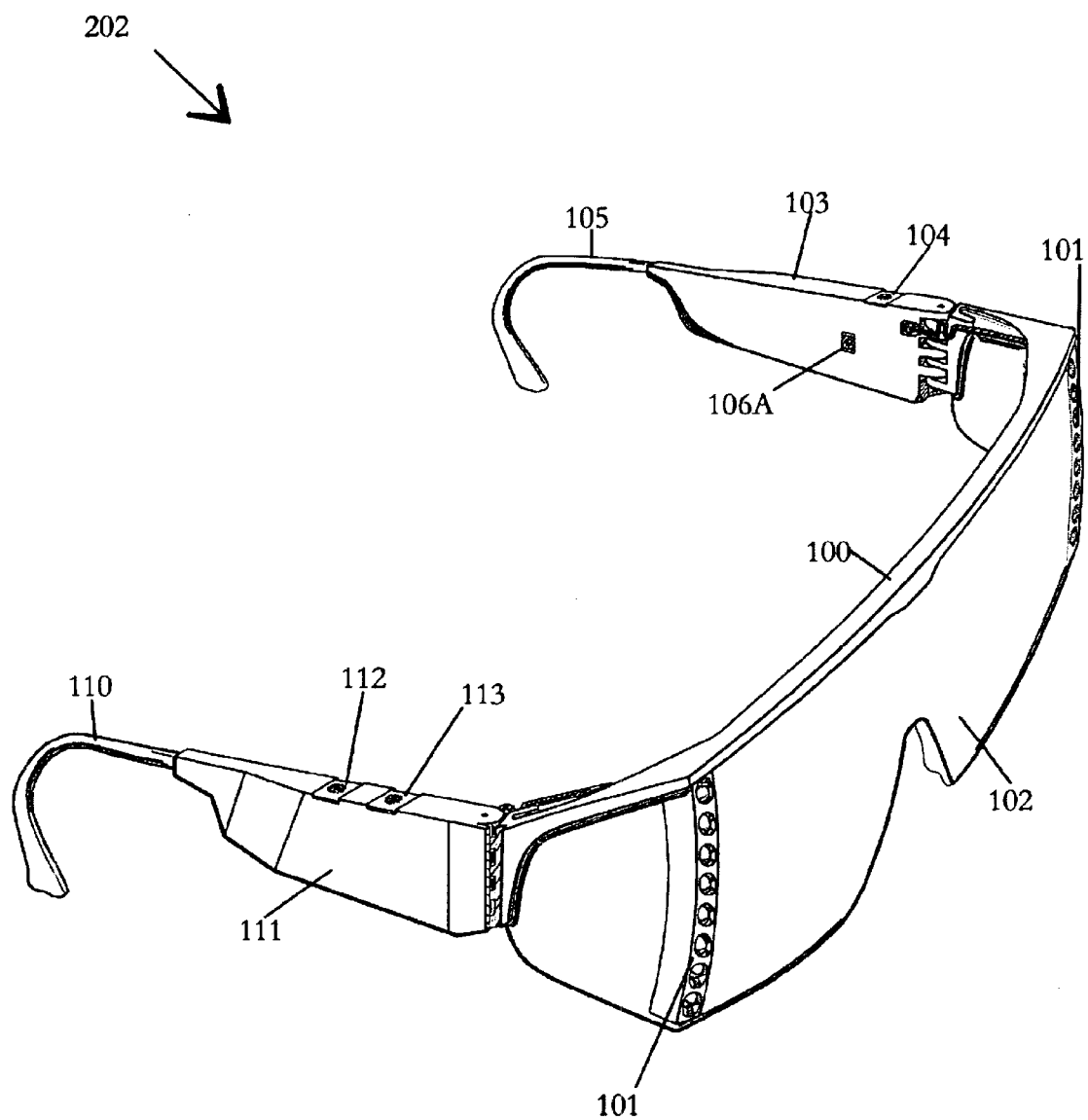
FIG. 1 is a perspective view of the present invention utilizing externally located lighting arrays and powered earpieces.

100 Frame for powered earpiece
100A Lens connecting lug
100B Lens connecting lug
101 External array
101A Right section of external array
101B Toe
101C Grommet shaped passthrough
101D Grommet shaped passthrough
101E Electrical plug
101F Electrical plug
101G Electric cabling
101H Strain relief
102 Ext. array lens
102A Recess
102B Recess
102C socket
102D Connecting notch
102E Connecting notch
103 Left powered earpiece case frame
103A Earpiece socket
103B Jack
103C connection point
104 Switch
104A Switch wiring
104B Latching switch circuit
105 Earpiece
106A Flexible membrane with embedded conductors
106B Separating bezel
106C Contacting board
106D Contacting board wiring
106E Embedded conductor
106F Embedded conductor
106G Conductor
106H Conductor
107 Connection and control board
107A Connection and control board wiring
107B Resistor
108 Battery
108A Battery wiring
109 Case cover
110 Earpiece
111 Right powered earpiece case frame
111A Earpiece socket
111B Jack
111C connection point
112 Switch
112A Switch wiring
112B Brightness level circuit
113 Switch
113A Switch wiring
113B Latching switch circuit
114 Connection and control board
114A Connection and control board wiring
114B Resistor
115 Battery
115A Battery wiring
116 Case cover
117 Lens for internal array embodiment
117A, 117B, 117C, 117D Mounting holes
118 Internal array
118D, 118C, 118D, 118E Bezel embodying shaped mounting ring
119 Example of existing glasses
120 Universal mount array embodiment
121 Embedded array lens embodiment -continued Drawings -- Reference Numerals 121A light shielding layer
121B Embedded wiring
121C Right connection point
121D Left connection point
122 Cradle section of charger
122A Cradle charger circuit board
122B Transformer
122C Rectifier
122D Charging circuit
123 Jack, male
123A Plug
123B Wire
124 Jack, female
125 Wire
126 External battery case circuit board
126A Battery
126B Resistor
126C Switch
126D Brightness level circuit
126E Switch
127 Clip
128 Hinge pin
128A Hinge pin
129 Protruding electrical charging connector
130 Example of existing prescription-style eyeglasses
131 Clip-on led array
132 Left clip-on frame
132A Right clip-on frame
132B Led enclosure
132C Led enclosure
132D Spring-loaded clip
132E Spring-loaded clip
133 Right side of array for metal-style eyeglasses frame
133A Wiring clip
133B Wiring to left side of array
133C Wiring to power source
133D Mounting bezel
133E Mounting Bezel
134 Left side of array for plastic-style eyeglasses frame
134A Diffusing lens
134B Wiring to right side of array
134C Wiring to power source
134D Mounting hole
134E Mounting hole
134F Mounting hole
135 Cable
200, 200A, 200B, 200C, 200D, 200E, 200F, 200G, 200H, 200I, 200J, 200K, 200L Light emitting diodes
201 Light emitting diode embedded glasses
202 Assembly of External array powered earpiece glasses
204 Connector assembly
205 Cradle charger assembly
206 Charger terminal disconnect assembly
207 External battery assembly
208 Clip-on array frame and array assembly
209 Metal prescription-style eyeglass frame and array assembly
210 Plastic prescription-style eyeglass frame and array assembly

DETAILED DESCRIPTION

FIGS. 1, 2, 3, 4, 5, 6, 8, 10, 12, 28, 29, 30, 31, 32, 34, 38—PREFERED EMBODIMENT

For purpose toward promoting an understanding of the principles of the invention, reference will now be made to the embodiments illustrated in the drawings. Specific language will be used to describe same. It will, nevertheless, be understood that no limitation of the scope of the invention is thereby intended, such alterations and further modifications of the illustrated device, and such further applications of the principles of the invention as illustrated herein being contemplated as would normally occur to one skilled in the art to which the invention relates.

Certain terminology is used in the following description for convenience only and is not limiting. The words "right", "left", "upper", "lower", "inside", "outside", and "in front of" designate the placement and location of components from the wearer's point of view. The word "wearer" is to mean a person wearing the illuminated safety glasses. The words "led" and "leds" are used throughout as a shortened term for "light emitting diode" and "light emitting diodes". The terminology includes the words above specifically mentioned, derivatives thereof and words of similar import.

Referring now to FIG. 1 of the drawing, device 202 is shown comprising a lens 102, an array 101 (see also FIG. 2), a frame 100, two battery cases 103 and 111, two earpieces 105 and 110.

As seen in FIG. 2, the left and right extents of array 101 are mounted to the lens 102 by means of a socket 102C into which the array toe 101B is fitted; the grommet shaped passthroughs 101C and 101D snap into the recesses 102A and 102B. The lens 102 attaches to the frame 100 by snapping the connecting notches 102D and 102E into lens connecting lugs 100B and 100A (see FIG. 3). The socket 102C and the recesses 102A and 102B are present on both sides of the lens 102. The array toe 101B and the grommet shaped passthroughs 101C and 101D are present on both sides of the array 101. The connecting notches 102D and 102E are present on both sides of the lens 102. The connecting lugs 100B and 100A are present on both sides of frame 100. The lens 102 and the frame 100 may be made of a polymer or any suitable material.

Figure 6:
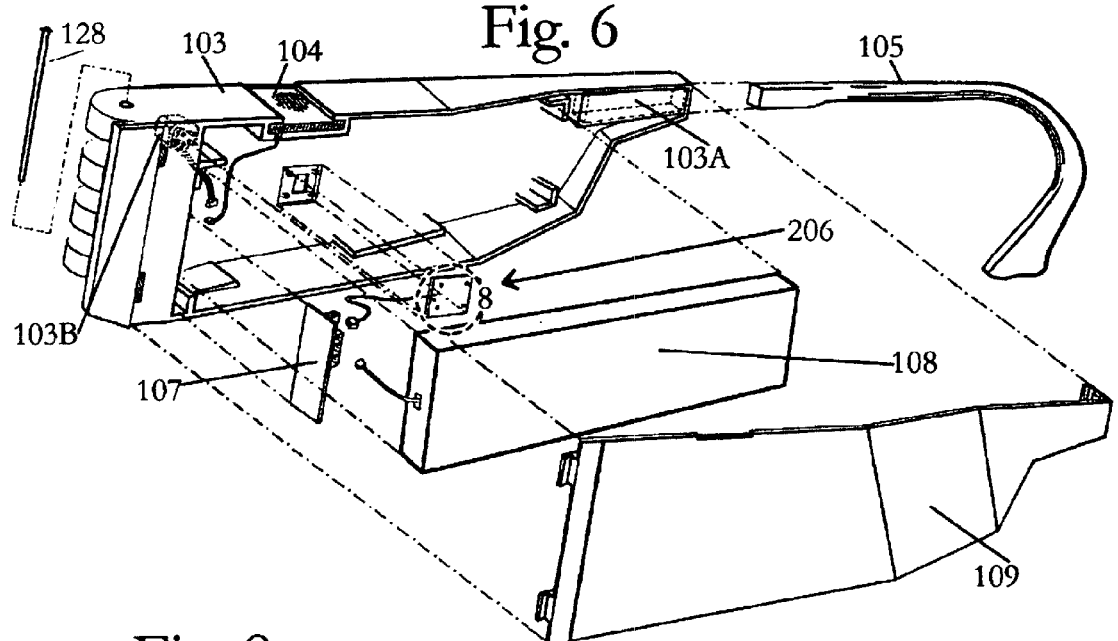
FIG. 6 is an exploded view of the left powered earpiece.

Referring now to FIG. 6 and FIG. 10, the powered case frames 103 and 111 attach to the frame 100 (see FIG. 2) by means of metal (or made of any suitable material) hinge pins 128 and 128A. The earpieces 105 and 110 insert into earpiece sockets 103A and 111A and are retained by force of friction. The powered case frames 103 and 111 and the earpieces 105 and 110 may be made of a polymer or any suitable material that inhibits electrical conduction.

Figure 5:
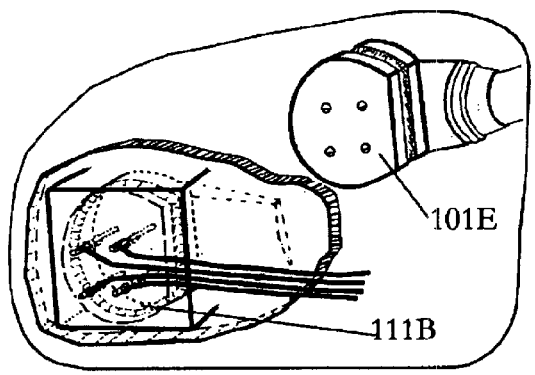
FIG. 5 is a magnified perspective view of the array's right electrical connector and a three-dimensional view of the right earpiece connecting jack.

The array electrical connectors 101 and 101F (see FIG. 2) connect to jacks 111B and 103B, these jacks integral and formed as a part of the case frames 103 and 111 and are made in such a way as to seal out liquid and gas (see also FIGS. 5 and 12).

Internal components common to both powered case frames 103 and 111 are batteries 108 and 115, connection and control boards 107 and 114, and switches 104 and 112. Mounted in powered case frame 103 is charging terminal disconnect assembly 206. Mounted in powered case frame 111 is switch 113. Case covers 109 and 116, preferably made of the same material as powered case frames 103 and 111, attach to powered case frames 103 and 111 in such a way as to seal out liquids and gasses. Batteries 108 and 115 preferably may be rechargeable lithium ion or may be of any suitable conventional or rechargeable type. Switches 104, 112, 113, and charging terminal disconnect assembly 206, are fashioned in such a way as to maintain the liquid and gas sealing properties of powered case frames 103 and 111.

Figure 8:
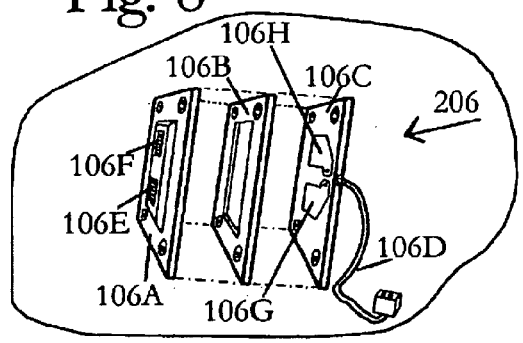
FIG. 8 is a magnified exploded view of components of the charger terminal disconnect assembly.

Referring now to the charging terminal disconnect assembly 206 depicted in FIG. 8, the flexible membrane 106A containing the embedded conductors 106E and 106F is separated from the contacting board 106C by separating bezel 106B. The protruding electrical charging connector 129 (see FIG. 29) provides the force to push the embedded conductors 106E and 106F into contact with the conductors 106G and 106H located on the contacting board 106C. The charging terminal disconnect assembly acts as a protection device, decoupling the electrical connection point (embedded conductors 1061E and 106F). It can also be used as a remote power connection (Discussed later).

Referring now to FIG. 28, the charger terminal disconnect assembly 206 of glasses 202, when present in the cradle charger assembly 205, is located to make contact with the protruding electrical charging connector 129. FIG. 29 shows the cradle section 122 of the cradle charger assembly 205 to illustrate the position of the protruding electrical charging connector 129.

External array 101 (see FIG. 2) is a one-piece cast, molded, or made by any suitable means component of the preferred embodiment. The material comprising the flexible body may be a flexible material such as a polymer or synthetic rubber or any other suitable material that inhibits electrical conduction. The electric cabling 101G is a plurality of separate conductors contained within the flexible body of array 101 and is present at all points in the array. Although part of array 101, for clarity, the electric cabling 101G is numerically identified with the number 101G at several points along the body of the array.

Referring to FIG. 4, the right section of array 101A is shown in cutaway view. A plurality of light emitting diodes 200 and in ascending alphabetical order to 200G, are positioned within the right section of array 101A. These leds may be aligned in various positions as to be useful in providing an illuminated area or areas beneficial to the wearer. They may be connected as a single or multiple parallel, series, or series/parallel circuit(s). They may be any solid state light source of any suitable wavelength, suitable case type, and capable of functions in addition to illumination. A larger part of each light emitting diode is contained within the flexible body; only the forward, light emitting portion of each light emitting diode is not encased within the body. The light emitting diodes 200 (and in ascending alphabetical order to 200G) are present in both sides of array 101. The strain relief 101H is also present at both sides of array 101.

The flexible body of array 101 encapsulates and insulates the means of electrical connection (including wiring 101G and plugs 101E and 101F) and the light emitting diodes (including 200 through 200G), acting as a barrier to liquids and gasses and absorbing physical shock. All arrays excepting array 121 (FIG. 24, to be discussed later) are also fashioned as a flexible body and although differently shaped, share these properties mentioned for array 101.

Figure 32:
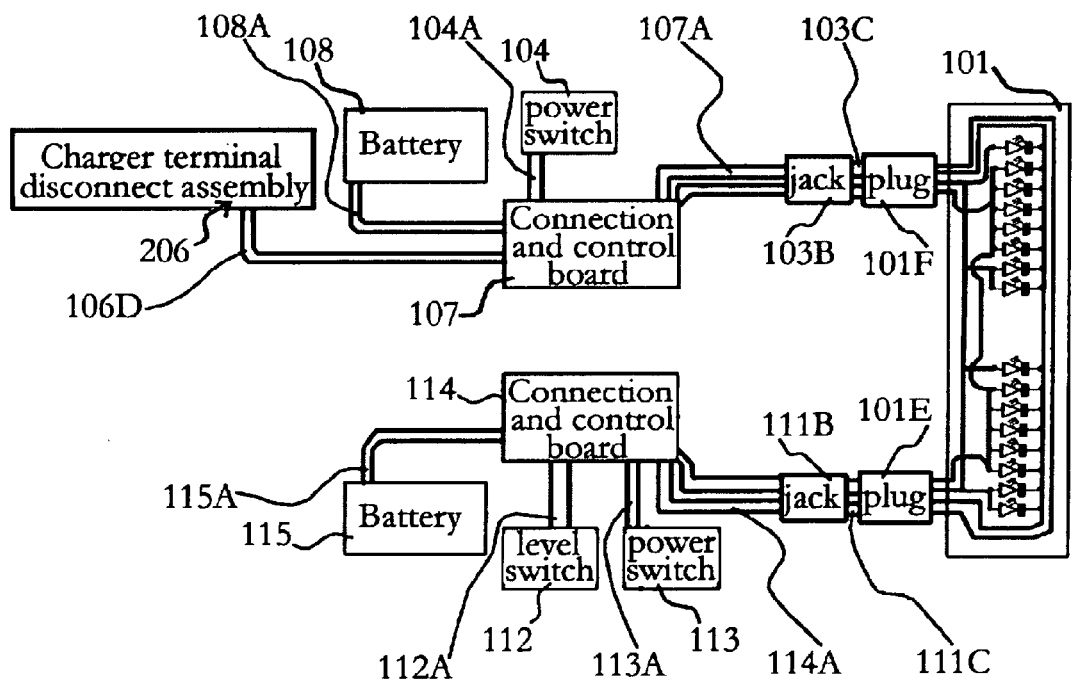
FIG. 32 is a diagram of the electrical components of the present invention.
Figure 34:
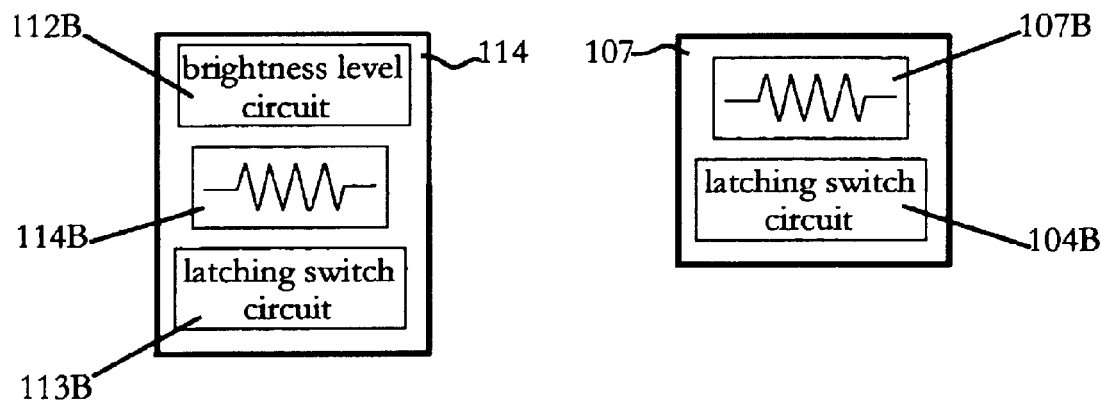
FIG. 34 is a diagram of circuit board functions.

Referring now to FIG. 32, showing the electronic component layout of the preferred embodiment. The connection and control board 107 is contained within powered case frame 103 (see FIG. 6) and connects by means of wiring to each of the following components also contained within powered case frame 103 (for clarity each component description separated by a semicolon): The charger terminal disconnect assembly 206 through wiring 106D; battery 108 through wiring 108A; power switch 104 through wiring 104A; jack 103B through wiring 107A.

Located at the left and right extents and Integral to array 101 are plugs 101F and 101E (see FIG. 2) each having a depression about their circumference (see FIG. 5). Plug 101F inserts into jack 103B, and plug 101E inserts into jack 111B. These plugs and jacks are fashioned to tightly interlock when connected for the purpose of repelling liquids and gasses from the conductors.

The charger terminal disconnect assembly 206 is the connection point for a recharging device such as cradle charger assembly 205 (FIG. 28) or any suitable charging device that may be employed to electrically connect to batteries 108 and 115.

Referring to FIG. 32, the pathway connecting the charger terminal disconnect assembly 206 to battery 108 is: from charger terminal disconnect assembly 206, through wiring 106D, through connection and control board 107, through wiring 108A to battery 108.

The pathway connecting the charger terminal disconnect assembly 206 to battery 115 is: from charger terminal disconnect assembly 206, through wiring 106D, through connection and control board 107, through wiring 107A, through jack 103B, through connection point 103C, through plug 101F, through array 101, through plug 101E, through connection point 111C, through jack 111B, through wiring 114A, through connection and control board 114, through wiring 115A, to battery 115.

Connection and control board 114 is contained within powered case frame 111 (FIG. 10) and connects by means of wiring to each of the following components also contained within powered case frame 111 (again, for clarity each component is separated by a semicolon):

The battery 115 through wiring 115A;
The brightness level switch 112 through wiring 112A;
The power switch 113 through wiring 113A;
The jack 111B through wiring 114A.

Located on connection and control board 114 may be a brightness level circuit 112B (see FIG. 34), which may be present as a potentiometer or a pulse width modulation circuit; both types of circuits are well known in the art; or any type of suitable circuit that allows wearer to adjust brightness of array 101 that may be employed. Switch 112 may be of any suitable type for the purposes of controlling the brightness level circuit 112B.

Latching switch circuit 113B may be any suitable circuit (as is well known in the art) that enables a momentary electronic state change (such as a resistance change, capacitance change, or voltage change) to effect a permanent change of state to another circuit. In operation, switch 113 may be a momentary switch where the purpose of pressing and releasing this switch is to create a momentary electrical change of state. This action will start voltage flow to a number of leds within array 101 (the leds this switch affects are now 'on' and will remain 'on'). Pressing and releasing switch 113 again will now stop the voltage flow to these leds in array 101 (led's are now 'off' and will remain 'off'). Resistor 114B may be employed to limit the amount of amperage flowing to the light emitting diode circuit it may control in array 101.

Located on connection and control board 107, and having the same properties as described for latching switch circuit 113B, may be latching switch circuit 104B. This additional switching circuit may, when activated by pressing power switch 104, activate a number of the light emitting diodes positioned within array 101 to illuminate (from the wearer's perspective) areas of peripheral vision, thus enabling the wearer to notice and react to objects not being directly gazed at (for example, useful while walking in the dark). Resistor 107B, located on connection and control board 107, may be employed to limit the amount of amperage flowing to the light emitting diode circuit it may control in array 101.

In other embodiments, switches 104 and 112 may control any number of leds contained within array 101, including but not limited to: leds of any suitable case type; leds illuminating areas other than directly ahead; leds of different types and colors; leds having an output above or below the visible light spectrum; leds capable of functions in addition to illumination.

If latching switch circuits 113B and 104B are not used, power switches 113 and 104 may be any suitable type of switch, preferably having a push-type latching function.

FIGS. 30 and 31 show components for external powering and charging of the preferred invention. The external battery case assembly 207 connects through use of a flexible casing containing conductors (wire 125) to cable 135 (connector 135 composed of a jack 123, flexible casing containing conductors 123B, and plug 123A), which in turn connects to either jacks 121C or 121D, located on embedded lens 121 (FIG. 24, to be discussed later), or by connector assembly 204 to charger terminal disconnect assembly 206 (FIG. 8) of illuminated safety glasses 202. The cable 135 is fashioned to be a barrier to liquids and gasses; flexible casing 123B electrically insulates the conductors and plugs 123A and 123 (all components of the assembly). The connector assembly 204 may also be fashioned of any suitable material that also repels conduction, liquids, and gasses from the encased plurality of conductors. Connector assembly 204 may also be used with any suitable charging device for the purpose of recharging batteries 108 and 115 (FIG. 32).

Figure 36:
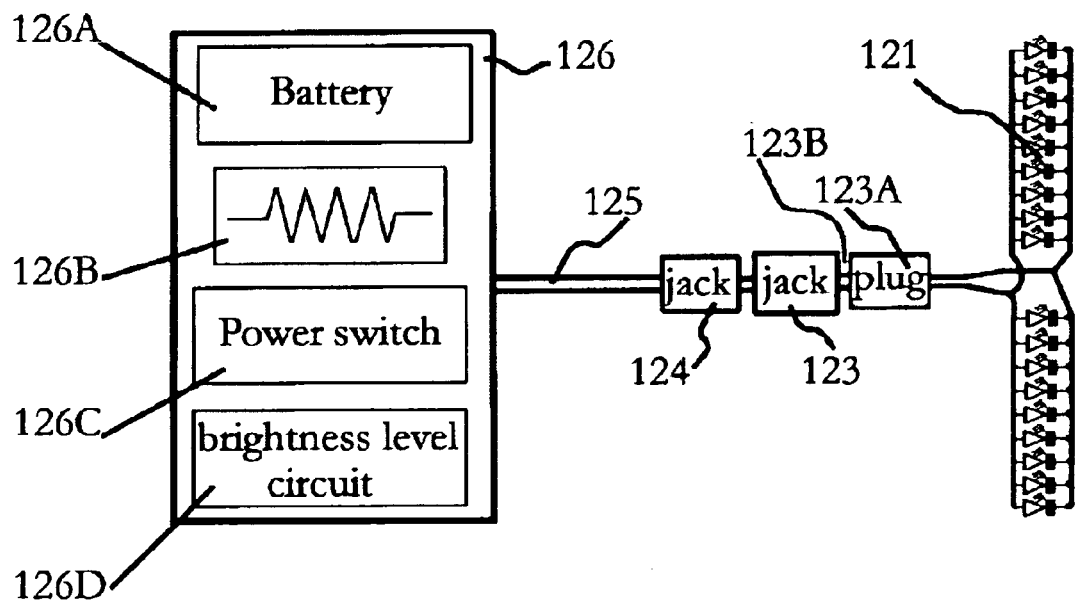
FIG. 36 is a diagram of the battery case electronics attached to the embedded array lens.

FIG. 36 shows the electronic component layout of the external battery case assembly 207 (FIG. 30). Circuit board 126 may contain battery 126A, resistor 126B, power switch 126C, and brightness level circuit 126D controlled by switch 126E (FIG. 30).

Battery 126A may be of any suitable conventional or rechargeable type.

Resistor 126B may be employed to limit the amount of amperage flowing to the light emitting diode circuit it may control.

Brightness level circuit 126D may be present as a potentiometer or a pulse width modulation circuit; both types of circuits are well known in the art; or any type of suitable circuit that allows wearer to adjust brightness of array 121. Switch 126E (FIG. 30) may be of any suitable type for the purposes of controlling the brightness level circuit 126D.

In addition to providing power to illuminated safety glasses 202, through use of cable made of conductors contained within a flexible casing (cable 135 (FIG. 30)), the external battery assembly 207 can provide power to other embodiments of the invention such as embedded lens 121 (FIG. 24).

Figure 38:
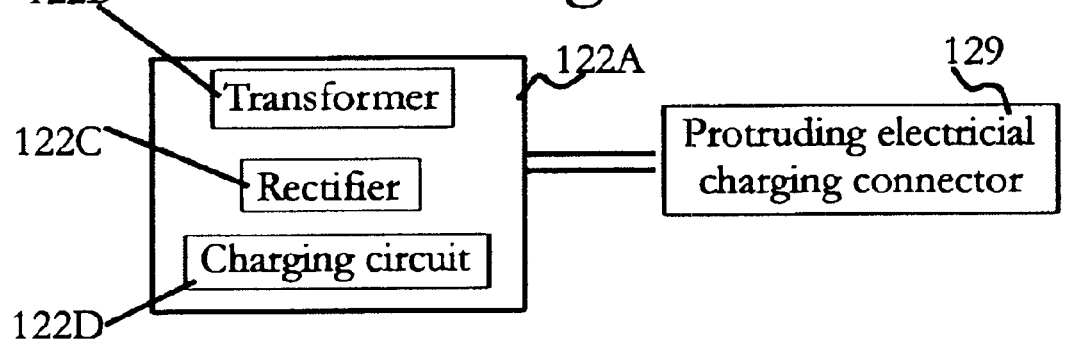
FIG. 38 is an electronic component diagram of the cradle charger.

Referring now to FIG. 38, showing the electronic component layout of a charging device for the preferred embodiment. The circuit board 122A contained within the cradle charger assembly 205 (FIG. 28) may employ a transformer 122B and rectifier 122C for the purpose of altering an AC input voltage (line voltage) in order to supply charging circuit 122D with a suitable DC voltage. The charging circuit 122D may be any suitable circuit designed for recharging batteries, as is well known in the art. The protruding electrical charging connector 129 (FIG. 29) provides means to conduct electricity through the charger terminal disconnect assembly 206 (FIG. 8) to the batteries 108 and 115 (FIG. 32) of illuminated safety glasses 202 (FIG. 28).

DETAILED DESCRIPTION—FIGS. 14, 16, 18, 20, 22, 24, 26, 30, 36, 40, 41, 42, 44, 46— ADDITIONAL EMBODIMENTS

An additional embodiment of the present invention is shown in FIGS. 14, 16, and 18. Array 118 is similar to array 101 (FIG. 2) in composition, function, and general form, but is present with these differences: The shape of the sections of array 118 containing the leds are shaped in order to facilitate internal mounting. Where array 101 attaches by use of a toe 101B and grommet shaped passthroughs 101C and 101D (refer to FIG. 2), array 118 does not have these shaped sections. Array 118 is present with bezels 118B through 118E. These flexible bezels are cylindrical in shape with a raised hemispherical section (see FIG. 18) around the circumference of the cylindrical section of each bezel. These shaped bezels secure array 118 to lens 117 by snapping into inversely shaped holes 117A to 117D (see FIG. 16) at the left and right front extents of lens 117. The material comprising the body of array 118 may be a flexible material such as a polymer or synthetic rubber or any other suitable material, and sharing the same electrical insulating and physical barrier properties as array 101 (FIG. 2). Within the flexible body of array 118 are positioned light emitting diodes 118B through 118E. These may be connected as a single or multiple parallel, series, or series/parallel circuit(s). They may be any solid state light source of any suitable wavelength, suitable case type, and capable of functions in addition to illumination.

FIG. 20 shows another embodiment of the present invention. Designed to adhere or otherwise affix to many presently available types of safety glasses 119, universal mount array 120 is cast or molded or made by any suitable means of a flexible material that gives the flexible body of array 120 the added property to conform and temporarily affix by any suitable means to different shapes of existing safety glasses. The flexible body of array 120 shares the same electrical insulating and physical barrier properties as array 101 (FIG. 2). The light emitting diodes contained in the flexible body of array 120 may also be connected as a single or multiple parallel, series, or series/parallel circuit(s). They may be any solid state light source of any suitable wavelength, suitable case type, and capable of functions in addition to illumination.

FIGS. 22, 24 and 26 show another embodiment of the present invention wherein glasses 201 are present with embedded array lens 121. Embedded array lens 121 is the body of the array. The material comprising the casting or molding (or made by any suitable means) of the lens may be a polycarbonate or other suitable transparent material that electrically and physically insulates the embedded components. Embedded into the lens are the right and left electrical connection points 121C and 121D present to provide powering access from either or both sides of the lens. Wiring 121B is present throughout the upper portion of lens. FIG. 26 shows a layer of light shielding 121A. This layer may be made of a heavily pigmented layer of any suitable material and is present to stop undesirable light transmission within the lens.

Led 200L is completely embedded within the lens, as are all of the leds contained in the lens. The leds contained in Embedded array lens 121 may be aligned in various positions as to be useful in providing an illuminated area beneficial to the wearer. The embedded leds may be any solid state light source and connected as a single or multiple parallel, series, or series/parallel circuit(s). They may be of any suitable wavelength and case type and may be capable of functions in addition to illumination.

FIG. 30 shows another embodiment of the invention. The battery case assembly 207 may be used to provide power to the arrays 118 (see FIG. 14) and 121 (see FIG. 24) through use of cable 135. Universal-mount array 120 (FIG. 20) may plug into jack 124. However; any suitable means of providing power to the arrays may be employed.

Figure 40:
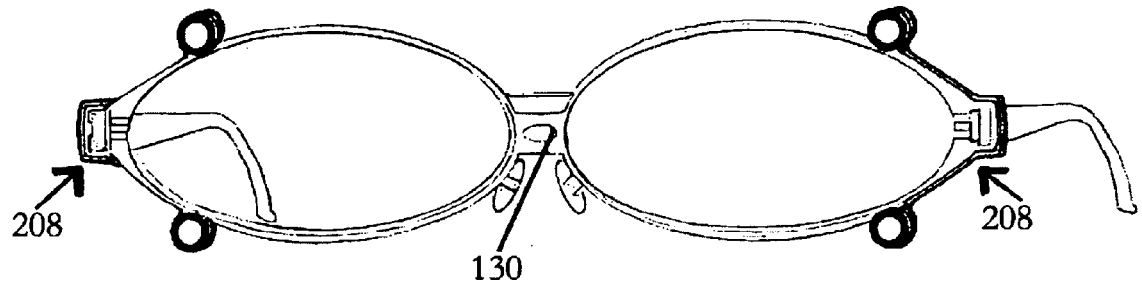
FIG. 40 is a perspective view of clip-on led array mounted on prescription-type eyeglass frames.
Figure 41:
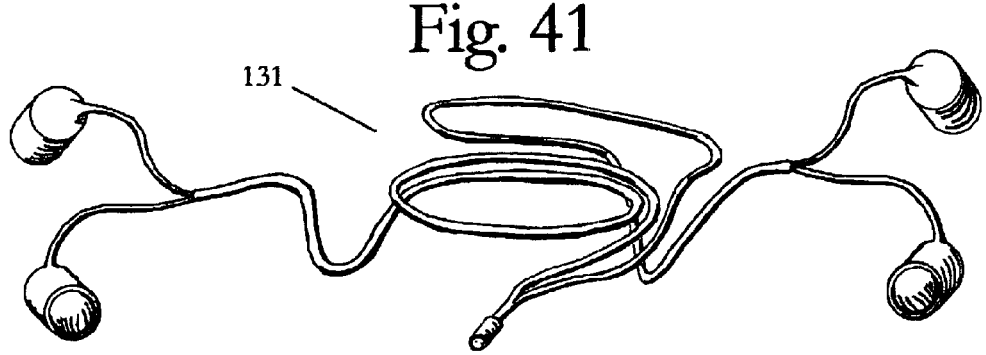
FIG. 41 is perspective view showing flexible body of array
Figure 42:
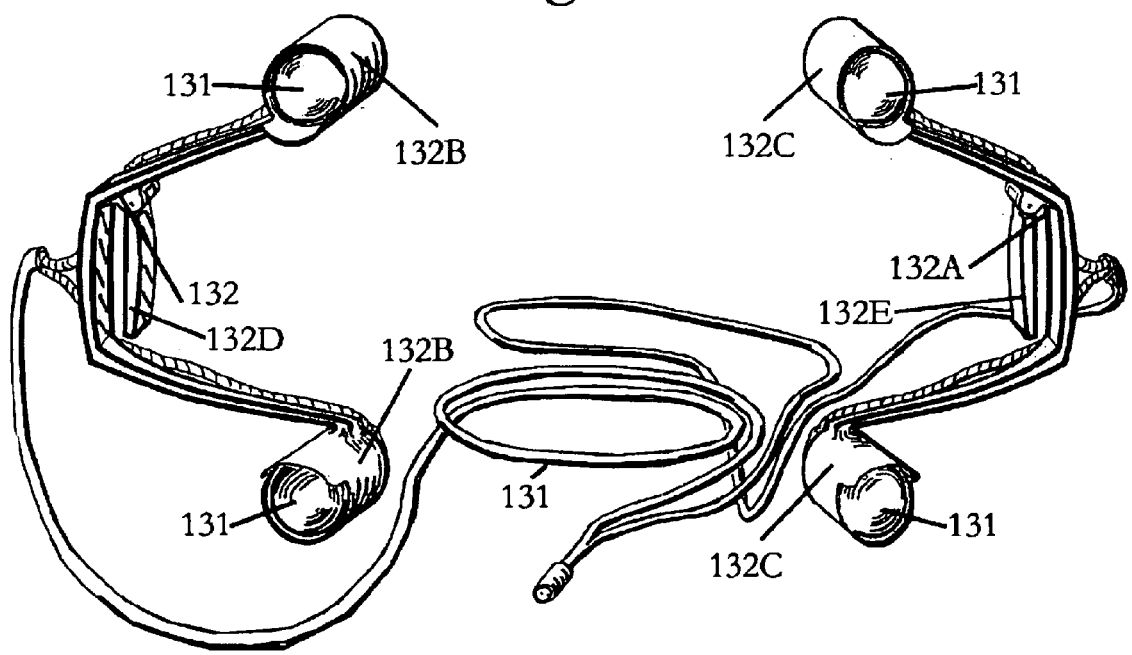
FIG. 42 is a perspective view of a clip-on led array.

FIG. 40 shows another embodiment of the invention. Clip-on type array assemblies 208 shown mounted on an example of presently available prescription-type frames 130. A perspective view of the assemblies 208 are shown in FIG. 42 where the led sections of the array 131 are installed into clip-on frames 132 and 132A. These frames may be comprised of metal or any suitable material, such as a polymer, that may be used. FIG. 41 shows array 131 un-mounted.

Array 131 is a one-piece body encasing all components that make up the array and is cast or molded or made by any suitable means. The led sections of the array may be any solid state light source and connected as a single or multiple parallel, series, or series/parallel circuit(s). They may be of any suitable wavelength and case type and may be capable of functions in addition to illumination. The flexible body of array 131 shares the same electrical insulating and physical barrier properties as array 101 (FIG. 2). The led sections of array 131 fit into the led enclosures 132B and 132C of clip-on frames 132 and 132A. Spring-loaded clips 132D and 132E provide means of attachment to an example of presently available frames 130, but any suitable means of attachment may be used.

Figure 44:
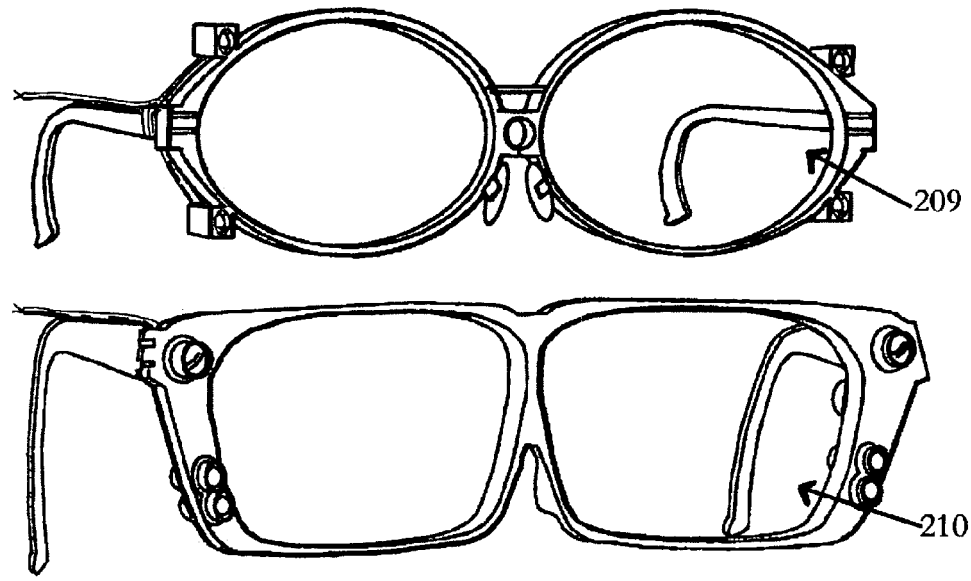
FIG. 44 is a perspective view showing different types of prescription-type frames made with mounting fixtures and mounted with led arrays.
Figure 46:
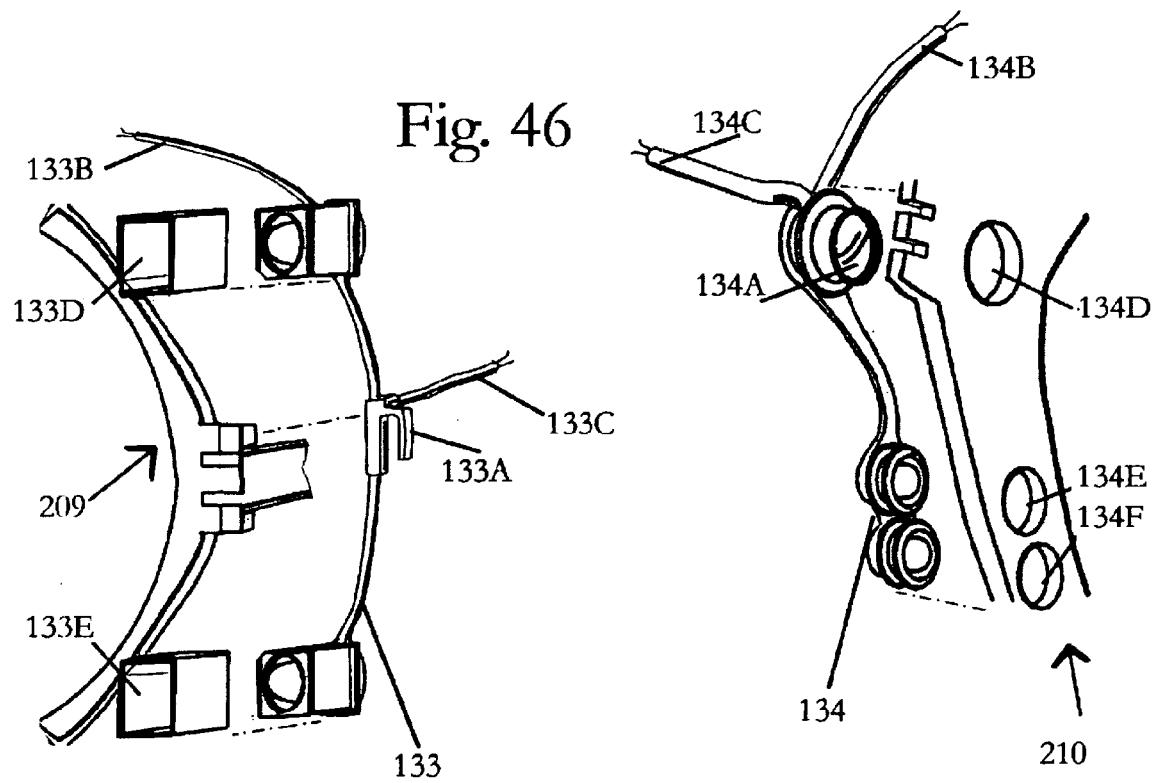
FIG. 46 is an exploded view showing different types of prescription-type frame arrays.

FIG. 44 is another embodiment of the invention showing metal-style 209 and plastic-style 210 prescription-type frames fashioned for use with led arrays. FIG. 46 illustrates how the arrays 133 and 134 attach to the assemblies 209 and 210.

The led sections of array 133 fit into the bezels 133D and 133E of frame assembly 209 and are held in place by means of friction. Wiring clip 133A, which is part of the flexible body of array 133, may also be present and will clip to the frame assembly 209.

The grommet shaped led sections of array 134 fit into the holes 134D, 134E, and 134F of frame assembly 210.

Arrays 133 and 134 are one-piece flexible bodies encasing the leds and the means of electrical connection and are cast, molded, or made by any suitable means. The flexible bodies of arrays 133 and 134 share the same electrical insulating and physical barrier properties as array 101 (FIG. 2). Additionally, arrays 133 and 134 may contain any solid state light source and be connected as a single or multiple parallel, series, or series/parallel circuit(s). They may be of any suitable wavelength and case type and may be capable of functions in addition to illumination.

Wiring 133B continues to the right side of array 133 and wiring 133C provides power to array 133.

Wiring 134B continues to the left side of array 134 and wiring 134C provides power to array 134. Additionally, array 134 includes diffusing lens 134A embedded within the body of array 134.

All embodiments of the arrays including array 101 (FIG. 2), array 118 (FIG. 16), array 120 (FIG. 20), array 121 (FIG. 24), array 131 (FIG. 41), array 133 (FIG. 46), and array 134 (FIG. 46) may also contain diffusing or other types of light modifying lenses or coverings encased as part of the array or attached by other means to the arrays.

Operation—FIGS. 1, 2, 6, 10, 16, 20, 24, 28, 30, 31, 41, 42, 46

The use of the illuminated safety/work glasses is a straightforward procedure. Two circuits of leds, operating independently and enclosed within array 101 (FIG. 2), are controlled by switches 104 (FIG. 5), 112, and 113 (FIG. 10). When the wearer needs or desires to use the illuminating feature of the glasses 202 (FIG. 1), pressing switch 113 (FIG. 10) will activate the leds it controls in array 101 (FIG. 2) and provide the desired illumination for the wearer.

Because the leds are positioned to both left and right, and above and below the wearer's eyes, and aligned to provide forward illumination, the leds activated by switch 113 (refer to FIG. 10) will provide shadow-free forward illumination.

If the wearer desires to adjust the brightness of the illumination, pressing switch 112 (any suitable control device may be used. For instance, a potentiometer actuated by a thumbwheel) will cause the brightness to vary. For the present discussion, a momentary switch 112 and time sensing circuit is used. The circuit reacts to the amount of time that switch 112 is pressed and changes the level of brightness while the switch is pressed. When the desired level of brightness is reached, releasing switch 112 stops this process and 'holds' at this level. It is envisioned that pressing the switch two times in quick succession will reset the level to full brightness. However; any suitable level controlling circuit may be employed, as is well known in the art.

When the wearer no longer needs the illumination, pressing switch 113 will turn off the leds it controls in array 101 (FIG. 2).

Switch 104 (FIG. 6) may control a number of leds within array 101 (FIG. 2). These leds may be aligned at any position as to provide suitable illumination, or may be of a different wavelength (color) and may be capable of functions other than illumination. For the present discussion, switch 104 (FIG. 6) controls leds that are aligned to provide separate areas of light that may be useful while walking at night. While the wearer is looking forward, these leds will illuminate downwards and upwards. This will allow the wearer, while looking forward, to notice and react to areas not being gazed at (areas of peripheral vision). These areas of illumination enable the wearer to notice possible obstructions (holes, tree branches, etc. . . . ) that otherwise may not be noticed while navigating at night. If the wearer desires this additional area to be illuminated, pressing switch 104 will activate the leds it controls and provide the desired illumination. Pressing switch 104 again will turn off these leds.

The glasses 202 (FIG. 1) may contain rechargeable batteries. To recharge the batteries, place the glasses in the cradle charger assembly 205 (FIG. 28). By using the connector assembly 204 (FIG. 6) any suitable type of charger may be used. In addition, the connector assembly 204 may be used to power the glasses 202 (FIG. 1) by connecting it to the external battery assembly 207 (FIG. 30) and glasses 202 (FIG. 1).

The external battery assembly 207 (refer to FIG. 30) is provided with switches 126C and 126D. The power switch is 126C and the brightness control switch is 126D. These controls may be of any suitable switch type in order to provide suitable control. Clip 127 allows means of securing the external battery assembly 207.

In operation, pressing switch 126C turns the array on and operation of switch 126D adjusts the brightness of the array.

The external battery assembly 207 may be used with cable 135 to provide power to glasses 201 (array 121 (FIG. 24)), array 118 (FIG. 16), array 120 (FIG. 20), array 131 (FIG. 42), array 133 and array 134 (FIG. 46).

Advantages:

From the description above, a number of advantages of my illuminated safety glasses become evident:

(a) Use of the glasses provides a hands-free, shadow-free light source for the wearer, whenever needed.

(b) Combines the features of separate devices (safety glasses and portable lighting) into one device. Combined, these features offer a better level of safety than just safety glasses alone, or just lighting alone. An example of this would be working under a vehicle where, while using the glasses for illumination, the wearer automatically gains eye protection from dust and debris. This extra protection is always present—when worn for eye protection, hands free lighting is always available, and when worn for illumination, eye protection is always present.

(c) Allows the wearer to use both hands for the task at hand. A task as simple as writing on a clipboard can become less simple when this task is performed in the dark—using the illuminating feature of the glasses negates having to juggle a pen, clipboard, and a flashlight. For more complex tasks, such as mechanical repair in the dark, or medical treatment in the dark (common situations for emergency medical technician situations), the user of these glasses will have needed lighting and the ability to use both hands for the task.

(d) Work in dark confined areas can be difficult, especially when the task necessitates being in prone positions. In these situations, a hardhat mounted with a lamp has the tendency to slip off the wearer's head, thus losing the ability to direct the lighting provided from the lamp. The glasses are much more secure than a hardhat mounted lamp and are not as susceptible to slipping off the wearer's head while used in these situations.

(e) Working in dark confined areas, the hardhat mounted headlamp or flashlight can cause shadowing or may physically obstruct the desired view. An example of this would be trying to look down the interior of a small diameter pipe. To illuminate the interior of the pipe, the lamp may have to be positioned directly above the opening, obstructing the view. Having the illumination source within the glasses dramatically reduces these shortfalls. The light source of the glasses are much closer to the eyes of the wearer, providing the ability to project useful light in extremely tight and confined areas.

(f) The ability to have within the array multiple circuits allows the wearer to use any or all of the light emitting diodes as needed. Additionally, the arrays can be manufactured for a variety of end uses providing different combinations of lighting areas, colors, or other useful, independently switched functions. Using leds, the frequency of the light can be tailored for specific purposes. For instance, if a pure white light is desired (useful for accurate color comprehension) in one circuit and a ultraviolet or other color of light in another circuit is also desired, the user can install an array combining these features into the glasses.

(g) The glasses are designed to be powered by different sources, and different types of batteries. The user can configure the glasses in such a way as to be most useful for the intended use. For example, the glasses may be self-contained, having rechargeable batteries mounted in the earpieces and recharged through use of a cradle charger. In other configurations, the glasses may be powered by a remote battery pack that provides power through use of a cable between the pack and the glasses. The batteries may be rechargeable or conventional batteries. Also, other array types may be used with the pack. Examples of this may be using the pack to provide power to a clip-on array mounted on presently available prescription type glasses or to prescription-type frames manufactured specifically for use with arrays.

(h) The placement, size and shape of the array is intended to provide a useful area and intensity of light for the wearer while not interfering (comparable to wearing existing plastic frame prescription-style eyeglasses) with areas of peripheral or forward vision. Further, the placement of the leds shields the wearer's eyes from the emanation point of the light. Also, the powered earpieces are designed to be a nominal weight while providing a suitable duration of power.

(i) The array is made without panels or circuit boards, and requires no mounting hardware. This allows the array to be flexible, minimizing the chances of interference of safety features built into existing safety glasses. In cases of-impact to the glasses the enclosed components will not create additional injury hazards to the wearer and the array can flex and absorb shock. Additionally, all components within the array including the leds, wiring connections and jacks are encased within the body of the array.

(j) The modular design of the glasses allows for replacement of assemblies within the glasses. For example, if a different array type is desired the user may replace the array without having to replace the complete assembly. If a lens is damaged, in the same manner as stated above, the user may replace the lens, frame, batteries, earpiece(s), etc. . . . . Embodiments of the glasses where the array is integral to the lens are an exception—the embedded lens would be replaced if a change of either component is desired.

(k) All the electrical components comprising the glasses are electrically insulated and are liquid and gas impermeable in order to be explosion proof. This feature allows the glasses to be used in potentially explosive environments. This feature also allows for ease of cleaning of the components if the glasses are used in areas where chemical or biological contamination may occur.

Conclusion, Ramifications, and Scope

Accordingly, the reader will see that compared to using the separate devices at the same time (i.e., using a lamp and wearing safety glasses) the illuminated safety glasses of the invention are more useful at providing utility and safety when combining the lamp and safety glasses as one device. Arrays designed to fit onto existing prescription-type glasses also offer a similar level of utility by enabling people to add the arrays to their glasses. Any situation where a flashlight is useful is a situation that can be improved through use of the present invention. Furthermore, the illuminated safety glasses have the additional advantages in that:

(a) The present invention permits the wearer to have portable illumination without the need for a flashlight or headlamp;

(b) The present invention enables the wearer to complete tasks without the need for an assistant to manipulate light for the wearer;

(c) The present invention utilizes long-lasting and rugged leds as the light source negating the need for a user to replace filament-type bulbs.

Although the description above contains many specificities, these should not be construed as limiting the scope of the invention but as merely providing illustrations of some of the presently preferred embodiments.

Thus the scope of the invention should be determined by the appended claims and their legal equivalents, rather than by the examples given.

What is claimed is:

1. Illuminated safety glasses for mounting on the head of the user, said illuminated safety glasses comprising:
   (a) a lens,
   (b) a flexible body,
   said flexible body comprising:
      (1) a substantially flexible electrically nonconductive material,
      (2) a plurality of light emitting diodes,
      (3) a plurality of electrical conductors, said substantially flexible electrically nonconductive material thereof encasing said plurality of light emitting diodes and said plurality of electrical conductors, said flexible body fashioned having an airtight electrical jack at a left extent and at a right extent of said flexible body, a portion of said plurality of electrical conductors electrically connecting said electrical jacks to said plurality of light emitting diodes, a remaining portion of said plurality of electrical conductors electrically connecting to said electrical jacks, said flexible body fashioned disposing a portion of said plurality of light emitting diodes at a left extent of said lens, to the left of, above and below user's eyes, and said flexible body fashioned disposing a remaining portion of said plurality of light emitting diodes at a right extent of said lens, to the right of, above and below users eyes, wherein a light emitting portion of said plurality of light emitting diodes being exposed from said flexible body in a forwardly facing direction, causing said plurality of light emitting diodes, when activated, and within a useful field of illumination of said plurality of light emitting diodes, to project said useful illumination onto viewable portion of an object or area viewable by user, and further providing said useful illumination on objects and areas viewable directly and peripherally by user, said substantially flexible electrically nonconductive material fashioned with an attaching means for removably attaching said flexible body to said lens, wherein the attachment of said flexible body to said lens unaffecting a predetermined structural performance of said lens, said substantially flexible electrically nonconductive material being an airtight seal for said plurality of electrical conductors and an embedded portion of said plurality of light emitting diodes, (c) a pair of earpieces,
(d) a frame,
    said frame having a first attachment means for removably attaching said frame to said lens,
    said frame having a second attachment means for removably attaching said frame to said earpieces,
(e) a remote power source,
    said remote power source comprising an airtight compartment containing:
        (1) at least one switch for enabling of the user to operate said power source,
        (2) at least one battery for providing electrical power to said plurality of light emitting diodes,
        (3) an electronic circuitry for brightness adjusting of said plurality of light emitting diodes within a useful illumination range,
        (4) an airtight electrical connection means for removably attachable electrical connecting of said circuitry to said plurality of light emitting diodes, whereby said flexible body and said electrical connection means being airtight for preventing the electrical structure from being an electrical ignition source in environments where flammable and explosive gasses and liquids are present, and whereby said flexible body, being temporarily substantially deformable to a predetermined amount, reducing user's risk of injury if said illuminated safety glasses experience a deforming impact, and whereby said illuminated safety glasses provide user with a multiple origin illumination source that, by directing light from above and below, and from the left and right of users eyes, and within said useful illumination range of said plurality of light emitting diodes, provides a substantial improvement over single and double origin head worn light sources by projecting said useful illumination onto viewable portion of a surface of an object or area viewed by user, and further simultaneously projecting useful direct and peripheral illumination for the user.

2. The illuminated safety glasses of claim 1 wherein said pair of earpieces further comprise:
    at least one internal airtight compartment, said internal airtight compartment for the containing of:
        (1) at least one rechargeable battery,
        (2) a electronic circuitry for brightness adjusting of said plurality of light emitting diodes,
        (3) a electronic circuitry for enabling recharging of said rechargeable battery,
        (4) at least one switch for enabling of user to operate said circuitry,
    said earpieces having a first airtight electrical connection means for removably attachable electrical connecting of said electronic circuitry for brightness adjusting to said plurality of light emitting diodes, and
    said earpieces having a second airtight electrical connection means for removably attachable electrical connecting of said electronic circuitry for enabling recharging to a remote electrical circuit.

3. The illuminated safety glasses of claim 1 wherein said plurality of light emitting diodes being selected from the group consisting of semiconductor light emitters.

4. A viewing lens device combining illumination and viewing functions, said viewing lens device comprising:
    (a) a viewing lens,
    (b) a plurality of light emitting diodes,
    (c) a plurality of electrical conductors,
    (d) a pair of electrical connection points embedded within a left and a right extent of said viewing lens,
    a portion of said plurality of electrical conductors electrically connecting said electrical connection points to said plurality of light emitting diodes, a remaining portion of said plurality of electrical conductors electrically connecting to said electrical connection points,
    a portion of said plurality of light emitting diodes being embedded within said left extent of said viewing lens, to the left of, above and below users eyes, and
    a remaining portion of said plurality of light emitting diodes being embedded within said right extent of said viewing lens, to the right of, above and below users eyes,
    wherein a light emitting portion of said plurality of light emitting diodes being oriented in a forwardly facing direction,
    causing said plurality of light emitting diodes, when activated, and within a useful field of illumination of said plurality of light emitting diodes, to project said useful illumination onto viewable portion of an object or area viewable by user, and further providing said useful illumination on objects and areas viewable directly and peripherally by user,
    said viewing lens being an airtight seal for said plurality of electrical conductors and said plurality of light emitting diodes,
    said viewing lens having an embedded light shielding means for preventing a undesirable light transmission from said plurality of light emitting diodes to a viewing portion of said lens.

5. The viewing lens device as recited in claim 4 wherein said plurality of light emitting diodes being selected from the group consisting of semiconductor light emitters.

6. An illumination providing device for mounting on existing head worn viewing devices, said illumination providing device comprising a flexible body, said flexible body comprising:
(a) a substantially flexible electrically nonconductive material,
(b) a plurality of light emitting diodes,
(c) a plurality of electrical conductors,
(d) an electrical jack, said substantially flexible electrically nonconductive material thereof encasing said plurality of light emitting diodes and said plurality of electrical conductors, said plurality of electrical conductors electrically connecting said electrical jack to said plurality of light emitting diodes, said electrical jack positioned at an extent of said flexible body, said electrical jack providing an airtight electrical connection means for transporting electricity from a power source to said plurality of light emitting diodes, said flexible body fashioned disposing a portion of said plurality of light emitting diodes at a left extent of said head worn viewing devices, to the left of, above and below user's eyes, and said flexible body fashioned disposing a remaining portion of said plurality of light emitting diodes at a right extent of said head worn viewing devices, to the right of, above and below users eyes, wherein a light emitting portion of said plurality of light emitting diodes being exposed from said flexible body in a forwardly facing direction, causing said plurality of light emitting diodes, when activated, and within a useful field of illumination of said plurality of light emitting diodes, to project said useful illumination onto viewable portion of an object or area viewable by user, and further providing said useful illumination on objects and areas viewable directly and peripherally by user, said flexible body including an adhesive removable attachment means for conformably attaching said flexible body to a exterior portion at said left and at said right extent of said head worn viewing devices, said substantially flexible electrically nonconductive material being an airtight seal for said plurality of electrical conductors and an embedded portion of said plurality of light emitting diodes, whereby user may mount said illumination providing device on an existing pair of glasses, and whereby said illumination providing device being airtight for preventing the electrical structure from being an electrical ignition source in environments where flammable and explosive gasses and liquids are present, and whereby said illumination providing device provides user with a multiple origin illumination source that, by directing light from above and below, and from the left and right of users eyes, and within said useful illumination of said plurality of light emitting diodes, provides a substantial improvement over single and double origin head worn light sources by projecting light onto viewable portion of a surface of an object or area viewed by user, and further simultaneously projecting useful direct and peripheral illumination for the user.

7. The illumination providing device for mounting on existing head worn viewing devices as recited in claim 6, further including a pair of removably attachable fixtures, wherein said portion of said flexible body containing said plurality of light emitting diodes being removably attachable to said pair of fixtures, said pair of fixtures having a removable attachment means for temporary attaching thereof to said left extent and said right extent of said head worn viewing devices.

8. The illumination providing device for mounting an existing head worn viewing devices as recited in claim 6 wherein said plurality of light emitting diodes being selected from the group consisting of semiconductor light emitters.

9. A prescription eyeglasses device combining the functions of containing prescription lenses and providing illumination for user, said prescription eyeglasses device comprising:

(1) a prescription eyeglasses frame,
(2) a flexible body, said flexible body comprising:
(a) a substantially flexible electrically nonconductive material,
(b) a plurality of light emitting diodes,
(c) a plurality of electrical conductors,
(d) an electrical jack, said prescription eyeglasses frame having a plurality of fittings, a portion of said flexible body encasing said plurality of light emitting diodes, wherein said plurality of fittings being fashioned to removably contain said portion of said flexible body encasing said plurality of light emitting diodes, said substantially flexible electrically nonconductive material encasing said plurality of electrical conductors, said plurality of electrical conductors electrically connecting said electrical jack to said plurality of light emitting diodes, said electrical jack positioned at an extent of said flexible body, said electrical jack providing an airtight electrical connection means for transporting electricity from a power source to said plurality of light emitting diodes, said portion of flexible body encasing said plurality of light emitting diodes fashioned disposing a portion of said plurality of light emitting diodes at a portion of said fittings at a left extent of said prescription eyeglasses frame, to the left of, above and below user's eyes, and said portion of flexible body encasing said plurality of light emitting diodes fashioned disposing a remaining portion of said plurality of light emitting diodes at a remaining portion of said fittings at a right extent of said prescription eyeglasses frame, to the right of, above and below users eyes, wherein a light emitting portion of said plurality of light emitting diodes being exposed from said flexible body in a forwardly facing direction, causing said plurality of light emitting diodes, when activated, and within a useful field of illumination of said plurality of light emitting diodes, to project said useful illumination onto viewable portion of an object or area viewable by user, and further providing said useful illumination on objects and areas viewable directly and peripherally by user, said substantially flexible electrically nonconductive material being an airtight seal for said plurality of electrical conductors and an embedded portion of said plurality of light emitting diodes, whereby user may removably mount said flexible body to said prescription eyeglasses frame, and whereby said flexible body being airtight for preventing the embedded electrical structure from being an electrical ignition source in environments where flammable and explosive gasses and liquids are present, and whereby said prescription eyeglasses frame combining the functions of containing prescription lenses and providing illumination for user, provides user with the ability to have corrected eyesight in combination with providing user with a multiple origin illumination source that, by directing light from above and below, and from the left and right of users eyes, and within said useful illumination of said plurality of light emitting diodes, provides a substantial improvement over single and double origin head worn light sources by projecting light onto viewable portion of a surface of an object or area viewed by user, and further simultaneously projecting useful direct and peripheral illumination for the user.

10. The flexible body for mounting on said prescription eyeglasses device as recited in claim 9 wherein said plurality of light emitting diodes being selected from the group consisting of semiconductor light emitters.

* * * * *